(12) United States Patent
Jeong et al.

(10) Patent No.: US 10,726,550 B2
(45) Date of Patent: Jul. 28, 2020

(54) METHOD FOR PROPOSING PERSONALIZED COSMETICS

(71) Applicant: Amorepacific Corporation, Seoul (KR)

(72) Inventors: Choon Bok Jeong, Yongin-si (KR); Se Jun Park, Yongin-si (KR); Yu Jin Kang, Yongin-si (KR); Kyung Ho Choi, Yongin-si (KR); Yeong Jin Choi, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 112 days.

(21) Appl. No.: 15/563,064

(22) PCT Filed: Mar. 30, 2016

(86) PCT No.: PCT/KR2016/003250
§ 371 (c)(1),
(2) Date: Sep. 29, 2017

(87) PCT Pub. No.: WO2016/159651
PCT Pub. Date: Oct. 6, 2016

(65) Prior Publication Data
US 2018/0342059 A1    Nov. 29, 2018

(30) Foreign Application Priority Data

Mar. 31, 2015 (KR) ........................ 10-2015-0045694

(51) Int. Cl.
*G06K 9/62*         (2006.01)
*G06T 7/00*         (2017.01)
(Continued)

(52) U.S. Cl.
CPC .............. *G06T 7/0014* (2013.01); *A61B 5/00* (2013.01); *A61B 5/1032* (2013.01); *A61B 5/441* (2013.01);
(Continued)

(58) Field of Classification Search
CPC ........ G06T 7/0014; G06T 2207/30088; G06Q 30/0631; A61K 8/18; G06K 9/6215
See application file for complete search history.

(56) References Cited

U.S. PATENT DOCUMENTS 6,437,866 B1    8/2002 Flynn
2010/0185064 A1    7/2010 Bandic et al.
(Continued)

FOREIGN PATENT DOCUMENTS

JP        10-339670 A     12/1998
JP      2004-209227 A      7/2004
(Continued)

OTHER PUBLICATIONS

International Search Report for PCT/KR2016/003250 dated Jul. 19, 2016 [PCT/ISA/210].
(Continued)

*Primary Examiner* — Solomon G Bezuayehu
(74) *Attorney, Agent, or Firm* — Sughrue Mion, PLLC

(57) ABSTRACT

The present invention provides a method for proposing personalized cosmetics and a system for implementing the same, the method comprising the steps of: photographing the visible spectrum of the skin of a subject to be measured; mapping a personalized visible spectrum to the measured visible spectrum of the skin so as to generate a spectral comparison table; matching a personalized composition to the spectral comparison table; and displaying the matched personalized composition on an image display unit.

13 Claims, 2 Drawing Sheets

(51) Int. Cl.
*A61B 5/00* (2006.01)
*G06Q 30/06* (2012.01)
*A61B 5/103* (2006.01)
*A61K 8/18* (2006.01)

(52) U.S. Cl.
CPC .............. *A61B 5/7246* (2013.01); *A61K 8/18* (2013.01); *G06K 9/6215* (2013.01); *G06Q 30/0621* (2013.01); *G06Q 30/0631* (2013.01); *G06T 2207/30088* (2013.01)

(56) References Cited

U.S. PATENT DOCUMENTS

| 2012/0321759 | A1* | 12/2012 | Marinkovich | G01N 21/55 |
| | | | | 426/231 |
| 2013/0300761 | A1* | 11/2013 | Ahmed | G01J 3/463 |
| | | | | 345/595 |
| 2013/0320855 | A1* | 12/2013 | Hulett | F21V 9/08 |
| | | | | 315/113 |
| 2014/0267609 | A1* | 9/2014 | Laffargue | H04N 13/20 |
| | | | | 348/46 |
| 2016/0106198 | A1* | 4/2016 | Yoshida | G01N 21/27 |
| | | | | 356/402 |
| 2016/0345887 | A1* | 12/2016 | Yoshida | A61B 5/4261 |
| 2017/0236019 | A1* | 8/2017 | Watson | G06K 9/2018 |
| | | | | 382/105 |

FOREIGN PATENT DOCUMENTS

JP  2012-215504 A  11/2012
KR  10-2014-0116429 A  10/2014

OTHER PUBLICATIONS

Written Opinion for PCT/KR2016/003250 dated Jul. 19, 2016 [PCT/ISA/237].

* cited by examiner

[FIG. 1]
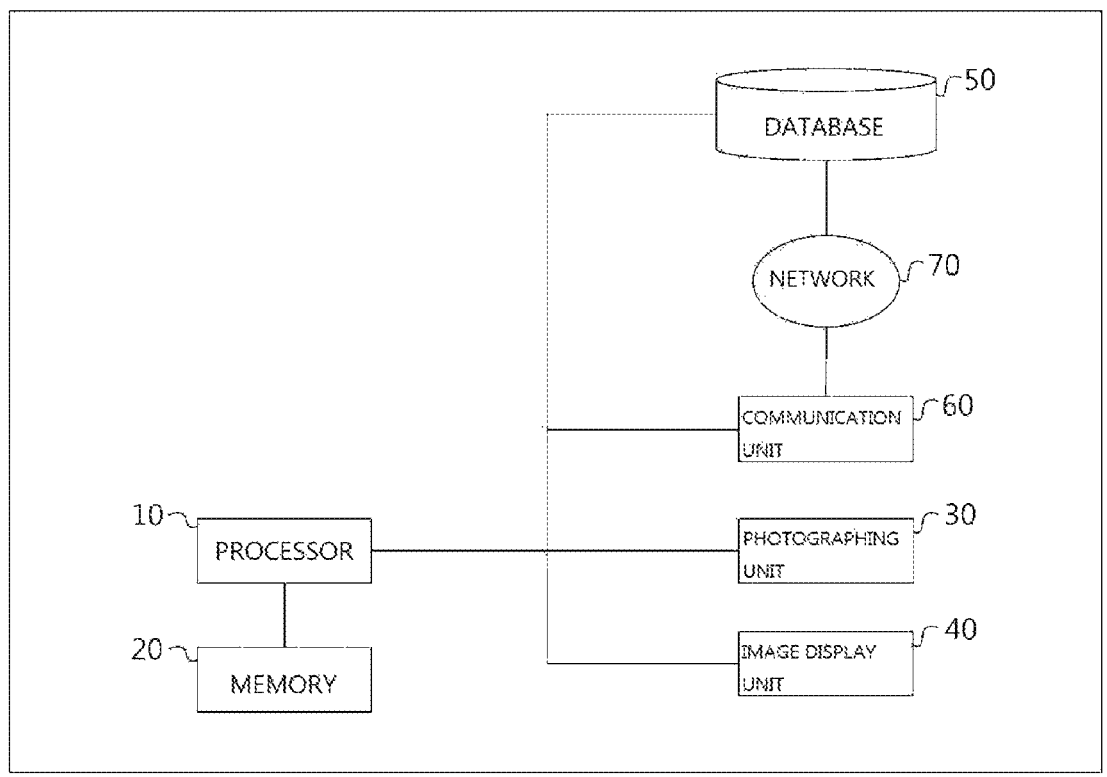

[FIG. 2]
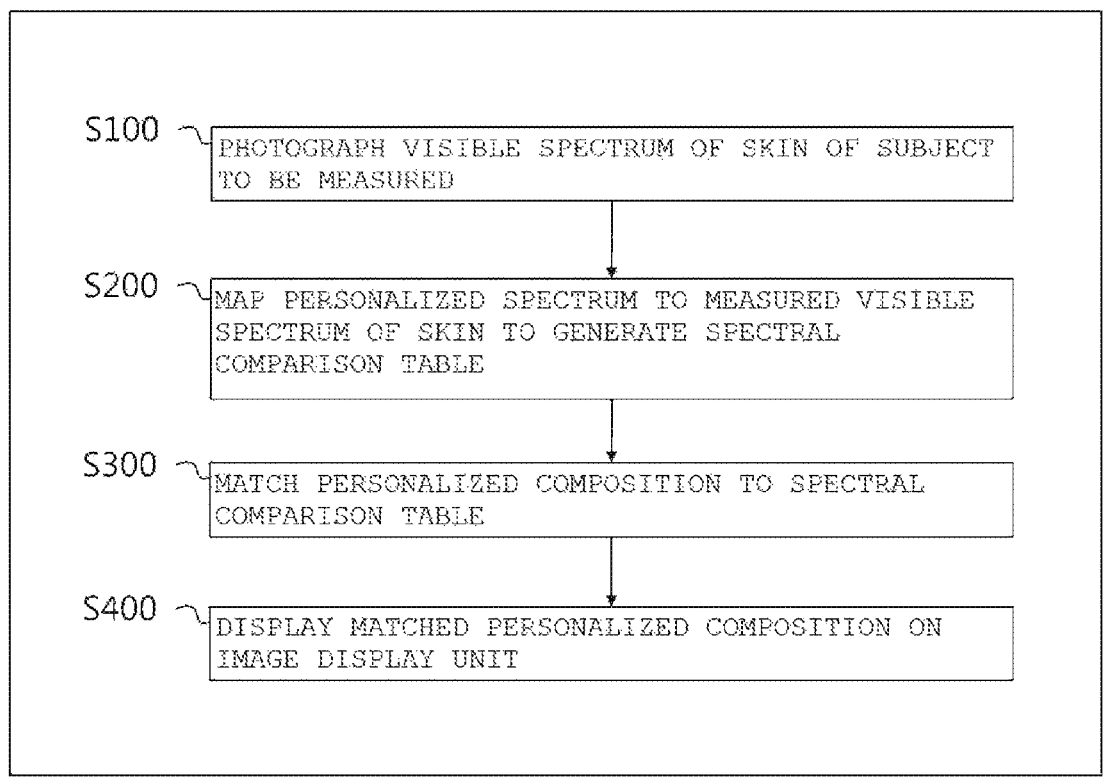

METHOD FOR PROPOSING PERSONALIZED COSMETICS

TECHNICAL FIELD

The present invention relates to a method for proposing personalized cosmetics and a system for performing the same.

This application claims the benefit of priority based on Korean Patent Application No. 10-2015-0045694, filed on Mar. 31, 2015 with the Korean Intellectual Property Office, the disclosure of which is incorporated herein by reference in its entirety.

BACKGROUND ART

The realization of ideal through cosmetics has become an important concern of customers. In order to satisfy these needs of customers, studies are performed in various manners, for example, by mimicking an ideal skin tone through skin color studies for each region or by correcting a skin tone through the expression of colors at a specific wavelength.

In particular, in customers using cosmetics, there is a high demand to appear for a skin to be not dry, and to moisturize a skin and so appear moist and bright, namely to express moisture feeling. In this regard, studies associated with skin change caused by moisture have been performed mainly as index such as moistness, trans-epidermal water loss (TEWL) in skin, or the like. However, the optical properties have only been studied extensively, for example, a skin applied with moisturizer looking darker than before application of the moisturizer, optical patterns being varied depending on the amount of moisture in vitro, or the like. The studies for accurately understanding the exact optical properties commonly shown by moisture and implementing the same are still not satisfactory.

In addition, studies according to a change in brightness has been performed by analyzing skin colors using an L, a, b color system, but a simple change of brightness was shown and hence information for mimicking properties was insufficient. In a color matching system of a makeup formulation that has been commonly used up to date, a method of expressing a color by adding yellow, red, and black pigments to a white base has been utilized. However, this method was not sufficient to accurately mimic a phenomenon where a particular color is highlighted while getting bright, which is an alteration in a spectrum positive (+) direction. In addition, the pigment may either have spectrums at particular peaks or combine them for expressing colors. Further, when a combination with another spectrum such as a skin color is generated, the pigment may be changed to an unexpected color.

Accordingly, a solution capable of proposing a cosmetic composition, which allows for mimicking a skin condition preferred according to the fashion, to be customized for a personal skin condition, by more accurate skin analysis and provision of a composition having a customized spectrum, compared to an existing method of optically analyzing skins, and a system capable of implementing the same are required.

DETAILED DESCRIPTION OF THE INVENTION

Technical Problem

Accordingly, the object of the present invention is to provide a method capable of proposing a cosmetic composition, which allows for mimicking various preferred skin conditions, to be customized for a personal skin condition, by more accurate skin analysis, compared to an existing method of optically analyzing skins, and a system capable of performing the above method.

Technical Solution

The present invention provides a method for proposing personalized cosmetics comprising the steps of: photographing a visible spectrum of a skin of a subject to be measured; generating a spectral comparison table by mapping a personalized visible spectrum to the measured visible spectrum of the skin; matching a personalized composition to the spectral comparison table; and displaying the matched personalized composition on an image display unit.

In addition, the present invention provides a system for proposing personalized cosmetic formulations, which comprises: a computer including a processor and a memory storing instructions for performing the following method by the processor, a photographing unit configured to photograph a visible spectrum of a skin of a subject to be measured, and an image display unit configured to display a proposal content of personalized cosmetics.

The method includes the steps of: photographing the visible spectrum of a skin of a subject to be measured by the photographing unit, generating a spectral comparison table in the memory by mapping a personalized visible spectrum to the measured visible spectrum of the skin, matching a personalized composition to the spectral comparison table, and displaying the matched personalized composition on the image display unit.

Advantageous Effects

A method for proposing personalized cosmetics and a system for performing the method according to the present invention can photograph the skin of a subject to be measured in the form of a visible spectrum and analyze the same in order to propose a cosmetic composition, which allows for mimicking various preferred skin conditions, to be suitable for the subject to be measured, i.e. to be customized. Furthermore, it is possible to propose a cosmetic product corresponding to the cosmetic composition.

In addition, it is possible to provide a predicted display image when the proposed cosmetic product is applied to the skin even though the product is not applied to the skin of the subject to be measured.

BRIEF DESCRIPTION OF DRAWINGS

FIG. 1 is a diagram illustrating a system according to an embodiment of the present invention.

FIG. 2 is a flowchart illustrating a proposed method according to an embodiment of the present invention.

BEST MODE FOR INVENTION

Reference will now be made in detail to embodiments of the present invention, examples of which are illustrated in the accompanying drawings. The present invention may, however, be embodied in different forms and should not be construed as limited to the embodiments set forth herein.

Hereinafter, a system for proposing personalized cosmetic formulations according to an embodiment of the present invention will be described in detail with reference to FIGS. 1 and 2.

FIG. 1 is a diagram illustrating the configuration and connection of the system for proposing personalized cosmetic formulations according to the embodiment of the present invention.

In the specification, all calculation steps may be performed by a processor 10.

In an embodiment of the present invention, a memory 20 stores corresponding instructions for performing respective steps of a proposal method according to the present invention processed by the processor 10.

The processor 10 may execute the instructions stored in the memory 20.

In an embodiment of the present invention, a photographing unit 30 may be a device that measures the spectrum of reflected light in a closed space, and may be specifically a product affiliated with model CM-2500d or CM2600d made by Konica Minolta Corporation.

In an embodiment of the present invention, the photographing unit 30 may include a device for photographing image data. The device for photographing image data may be independent from a device for photographing a visible spectrum, and may also photograph the visible spectrum.

A database 50 may be directly connected to the processor 10, or may be connected to a network 70 through a communication unit 60 connected to the processor 10.

An input unit 80 may be integral with an image display unit 40, and may be specifically a touch screen type.

The image display unit 40 is not limited as long as it may electronically display an image.

The method for proposing personalized cosmetics according to an embodiment of the present invention will be described in detail below.

FIG. 2 is a flowchart illustrating an example of steps S100 to S400 in the method for proposing personalized cosmetics according to the embodiment of the present invention.

In the embodiment of the present invention, the method further includes a step of selecting a personalized visible spectrum (S010).

The step of selecting a personalized visible spectrum (S010) may be input through the input unit 80 connected to the processor 10.

The personalized visible spectrum may be at least one preset stored in the memory 20 or the database 50.

FIG. 1 illustrates the system according to the embodiment of the present invention.

The preset of the personalized visible spectrum may be a moisture glow-mimicking spectrum, a shine-mimicking spectrum, a skin color-complementing spectrum, or a milky-color-mimicking spectrum.

The moisture glow-mimicking spectrum refers to a patterned spectrum that appears in a state in which a skin is moisture-supersaturated, and is particularly a visible spectrum in a state in which a skin is moisture-oversaturated.

The shine-mimicking spectrum is a patterned spectrum that appears in a state in which a skin is oil-supersaturated.

The skin color-complementing spectrum is a patterned spectrum that appears in a state in which the intensity in a red wavelength range is reinforced.

The milky-color-mimicking spectrum is a patterned spectrum that appears when a yellow wavelength is reduced in a state in which the intensity in an overall wavelength range is reinforced.

In addition, the preset of the personalized visible spectrum may be a spectrum obtained by performing a step of photographing a standard group of skin conditions preferred according to the fashion to calculate a mean intensity value for each wavelength.

In an embodiment of the present invention, the step of selecting a personalized visible spectrum (S010) may be performed before a step of photographing a visible spectrum of a skin of a subject to be measured (S100) or a step of generating a spectral comparison table (S200).

In an embodiment of the present invention, the step of photographing a visible spectrum of a skin of a subject to be measured (S100) includes photographing the visible spectrum of the skin of the subject to be measured by the photographing unit 30.

In an embodiment of the present invention, the step of generating a spectral comparison table (S200) includes a step of comparing the measured visible spectrum of the skin with the personalized visible spectrum for each wavelength range thereof and of storing a data pair (W, I) in the spectral comparison table (S210). The "W" of the data pair refers to a wavelength range, and the "I" of the data pair refers to a difference value between the intensity of the personalized visible spectrum and the intensity of the measured visible spectrum of the skin in the "W".

In an embodiment of the present invention, the W of the data pair includes a data pair (WMAX, WMIN). The "WMAX" refers to an upper limit value of the visible wavelength, and the "WMIN" refers to a lower limit value of the visible wavelength.

In an embodiment of the present invention, in the step of storing a data pair (W, I) in the spectral comparison table (S210), a difference between the integral value of the intensity of the personalized visible spectrum and the integral value of the intensity of the measured visible spectrum of the skin is stored in the "I" in the wavelength range of WMIN to WMAX of the data pair.

In an embodiment of the present invention, the step of storing a data pair (W, I) in the spectral comparison table (S210) further includes a step in which a difference between the integral value of the intensity of the personalized visible spectrum and the integral value of the intensity of the measured visible spectrum of the skin is stored in a data item $I_{all}$ in the overall visible wavelength range.

In an embodiment of the present invention, the wavelength range of the personalized visible spectrum may be, for example, 360 nm to 740 nm.

In an embodiment of the present invention, when the personalized visible spectrum selected in the step of selecting a personalized visible spectrum (S010) is a moisture glow-mimicking spectrum, the wavelength range of the personalized visible spectrum may be, for example, 360 nm to 550 nm.

In an embodiment of the present invention, a step of matching a personalized composition to the spectral comparison table (S300) includes a step of matching a component of the personalized composition to at least one data pair (W, I) stored in the spectral comparison table (S310).

In an embodiment of the present invention, the step of matching a component of the personalized composition (S310) includes a step of storing a component matched to a data item $C_{omponent}$ connected to the data pair (W, I).

In an embodiment of the present invention, the step of matching a component of the personalized composition (S310) includes matching a corresponding wavelength reinforcement material to the "W" of the at least one data pair (W, I) stored in the spectral comparison table.

In the specification, the wavelength reinforcement material means a material that increases a spectral intensity in a particular visible wavelength range of a skin by reflected light of the material when the material is applied to the skin.

In an embodiment of the present invention, the wavelength reinforcement material is one wavelength reinforcement powder or two or more wavelength reinforcement composite powders.

The wavelength reinforcement powder or each of the wavelength reinforcement composite powders may be one selected from the group consisting of mica, synthetic mica, alumina, borosilicate powder, talc, and sericite.

The wavelength reinforcement powder or wavelength reinforcement composite powder may be coated with one selected from the group consisting of titanium dioxide, iron oxide, and tin oxide.

The wavelength reinforcement powder or wavelength reinforcement composite powder may have a mean grain size of 2 to 16 µm.

Hereinafter, the description of the step of matching a component of the personalized composition (S310) is the same as the description given in the case where the moisture glow-mimicking spectrum is selected as the personalized visible spectrum.

In an embodiment of the present invention, the step of matching a component of the personalized composition (S310) includes a step of matching a violet wavelength reinforcement material as the component of the personalized composition when the "W" of the at least one data pair (W, I) stored in the spectral comparison table is 360 nm to 430 nm (S311).

The violet wavelength reinforcement material may be a model Sharon Soft Focus Violet made by CQV Corporation.

In an embodiment of the present invention, the step of matching a component of the personalized composition (S310) includes a step of matching a blue wavelength reinforcement material as the component of the personalized composition when the "W" of the at least one data pair (W, I) stored in the spectral comparison table is 440 nm to 490 nm (S312).

The blue wavelength reinforcement material may be a model Sharon Soft Focus Blue made by CQV Corporation.

In an embodiment of the present invention, the step of matching a component of the personalized composition (S310) includes a step of matching a green wavelength reinforcement material as the component of the personalized composition when the "W" of the at least one data pair (W, I) stored in the spectral comparison table is 500 nm to 570 nm (S313).

The green wavelength reinforcement material may be a model Sharon Soft Focus Green made by CQV Corporation.

In an embodiment of the present invention, the step of matching a component of the personalized composition (S310) includes a step of matching a yellow wavelength reinforcement material as the component of the personalized composition when the "W" of the at least one data pair (W, I) stored in the spectral comparison table is 580 nm to 590 nm (S314).

The yellow wavelength reinforcement material may be a model Sharon Soft Focus Yellow made by CQV Corporation.

As described above, the explanation of the step of matching a component of the personalized composition (S310) is the same as that in the case where the moisture glow-mimicking spectrum is selected as the personalized visible spectrum.

In an embodiment of the present invention, the method further includes a step of matching a content of the matched component of the personalized composition (S320) after the step of matching a component of the personalized composition (S310).

In an embodiment of the present invention, the step of matching a content of the matched component of the personalized composition (S320) includes a step of storing the content of the component matched to a data item $C_{ontent}$ connected to the data item $C_{omponent}$.

In an embodiment of the present invention, the step of matching a content of the matched component of the personalized composition (S320) is to match a value, obtained by multiplying the ratio value of the "I" of the data pair (W, I) to the data item $I_{all}$ by a correction factor, to the matched content of the component of the personalized composition, which may be expressed by the following Equation 1.

$$(W \text{ of data pair } (W,I))/(I_{all}) \times \text{correction factor} \qquad \text{[Equation 1]}$$

In an embodiment of the present invention, the step of matching a personalized composition to the spectral comparison table (S300) further includes a step of matching a personalized product by searching the matched component of the personalized composition from the personalized product database 50 (S330).

In the embodiment of the present invention, the step of matching a personalized product (S330) includes searching the matched component of the personalized composition together with the content thereof.

In an embodiment of the present invention, a step of displaying the matched personalized composition on the image display unit 40 (S400) displays the matched personalized product together on the image display unit 40. This should be interpreted to include displaying the matched personalized product on the image display unit 40 without displaying the matched personalized composition on the image display unit 40.

In an embodiment of the present invention, the step of photographing a visible spectrum of a skin of a subject to be measured (S100) further includes a step of photographing image data of the skin of the subject to be measured by the photographing unit 30 (S110).

In the embodiment of the present invention, the step of matching a personalized composition to the spectral comparison table (S300) further includes a step of converting the at least one data pair (W, I) stored in the spectral comparison table into a portion value (R, G, B) of the photographed image data to apply the same by the processor 10 (S320).

The step of converting the at least one data pair (W, I) into a portion value (R, G, B) of the photographed image data to apply the same (S320) may be performed in such a manner that the processor 10 calls a command set having a wavelength-RGB conversion filter algorithm stored in the memory 20.

The wavelength-RGB conversion filter algorithm may be a wavelength-RGB conversion filter algorithm that is commonly used in the art, and may be, for example, an algorithm FROM WAVELENGTH TO RGB FILTER (U.P.B. Sci. Bull., Series D, Vol. 69, No. 2, 2007) by Dragos Mihai, et al.

In an embodiment of the present invention, the step of displaying the matched personalized composition on the image display unit 40 (S400) further includes a step of displaying the converted and applied image data together (S410). It is possible to check the converted and applied image data on the image display unit 40 by the subject to be measured and to provide information for visually predicting a proposed personalized composition after application thereof.

The invention claimed is:

1. A method for proposing a personalized cosmetic composition, comprising the steps of:

photographing a visible spectrum of a skin of a subject to be measured to prepare a measured visible spectrum of the skin;

generating a spectral comparison table by mapping a personalized visible spectrum to the measured visible spectrum of the skin;

matching a personalized cosmetic composition to the spectral comparison table; and displaying the matched personalized cosmetic composition on an image display unit, wherein the personalized visible spectrum is a preset obtained by performing a step of photographing a standard group of skin conditions preferred according to a fashion to calculate a mean intensity value for each wavelength, wherein the step of generating a spectral comparison table comprises storing a data pair comprising W and I in the spectral comparison table by comparing the measured visible spectrum of the skin with the personalized visible spectrum for each wavelength range thereof, wherein the W of the data pair refers to a wavelength range, and wherein the I of the data pair refers to a difference value between an intensity of the personalized visible spectrum and an intensity of the measured visible spectrum of the skin in the W, wherein the step of matching a personalized cosmetic composition to the spectral comparison table includes matching a component of the personalized cosmetic composition to at least one data pair stored in the spectral comparison table, wherein the step of matching a component of the personalized cosmetic composition includes matching a corresponding wavelength reinforcement material to the W of the at least one data pair stored in the spectral comparison table, and wherein the wavelength reinforcement material is one wavelength reinforcement powder or two or more wavelength reinforcement composite powders which selected from the group consisting of mica, synthetic mica, alumina, borosilicate powder, talc, and sericite.

2. The method according to claim 1, wherein the personalized visible spectrum is at least one preset spectrum selected from the group consisting of a moisture glow-mimicking spectrum, a shine-mimicking spectrum, a skin color-complementing spectrum, and a milky-color-mimicking spectrum, and obtained by performing a step of photographing a standard group of preferred skin conditions according to make-up trend to calculate a mean intensity value for each wavelength, in which:
the moisture glow-mimicking spectrum refers to a patterned spectrum that appears in a state in which a skin is moisture-supersaturated, the shine-mimicking spectrum is a patterned spectrum that appears in a state in which a skin is oil-supersaturated, the skin color-complementing spectrum is a patterned spectrum that appears in a state in which the intensity in a red wavelength range is reinforced, and the milky-color-mimicking spectrum is a patterned spectrum that appears when a yellow wavelength is reduced in a state in which the intensity in an overall wavelength range is reinforced.

3. The method according to claim 1, wherein the wavelength range of the personalized visible spectrum is 360 nm to 740 nm.

4. The method according to claim 1, wherein the step of matching a component of the personalized cosmetic composition includes matching a violet wavelength reinforcement material as the component of the personalized cosmetic composition when the W of the at least one data pair stored in the spectral comparison table is 360 nm to 430 nm.

5. The method according to claim 1, wherein the step of matching a component of the personalized cosmetic composition includes matching a blue wavelength reinforcement material as the component of the personalized cosmetic composition when the W of the at least one data pair stored in the spectral comparison table is 440 nm to 490 nm.

6. The method according to claim 1, wherein the step of matching a component of the personalized cosmetic composition includes matching a green wavelength reinforcement material as the component of the personalized cosmetic composition when the W of the at least one data pair stored in the spectral comparison table is 500 nm to 570 nm.

7. The method according to claim 1, wherein the step of matching a component of the personalized cosmetic composition includes matching a yellow wavelength reinforcement material as the component of the personalized cosmetic composition when the W of the at least one data pair stored in the spectral comparison table is 580 nm to 590 nm.

8. The method according to claim 1, wherein the step of storing a data pair in the spectral comparison table further comprises storing a difference between an integral value of the intensity of the personalized visible spectrum and an integral value of the intensity of the measured visible spectrum of the skin in a data item in an overall visible wavelength range, the step of matching the personalized cosmetic composition to the spectral comparison table further includes matching a content of the matched component of the personalized cosmetic composition, and the step of matching a content of the matched component of the personalized cosmetic composition includes matching a value, obtained by multiplying a ratio value of the I of the data pair to the data item by a correction factor, to the matched content of the component of the personalized cosmetic composition.

9. The method according to claim 1, wherein the step of matching a personalized cosmetic composition to the spectral comparison table further includes matching a personalized product by searching the matched component of the personalized cosmetic composition from a personalized product database.

10. The method according to claim 9, wherein the step of matching a personalized product includes searching the matched component of the personalized cosmetic composition together with a content thereof.

11. The method according to claim 9, wherein the step of displaying the matched personalized cosmetic composition on an image display unit includes displaying the matched personalized product together on the image display unit.

12. The method according to claim 1, wherein the step of photographing a visible spectrum of a skin of a subject to be measured further includes photographing image data of the skin of the subject to be measured, the step of matching the personalized cosmetic composition to the spectral comparison table further includes converting the at least one data pair stored in the spectral comparison table into a portion value comprising R, G and B of the photographed image data to apply the same, and the step of displaying the matched personalized cosmetic composition on an image display unit further includes displaying the converted and applied image data together.

13. A system for proposing a personalized cosmetic formulation, comprising:
a computer including a processor and a memory storing instructions for performing the following method by the processor;
a photographing unit configured to photograph a visible spectrum of a skin of a subject to be measured to prepare a measured visible spectrum of the skin; and
an image display unit configured to display a proposal content of personalized cosmetic formulation,
wherein the method comprises:
photographing the visible spectrum of the skin of the subject to be measured by the photographing unit;
generating a spectral comparison table in the memory by mapping a personalized visible spectrum to the measured visible spectrum of the skin;
matching a personalized cosmetic formulation to the spectral comparison table; and
displaying the matched personalized cosmetic formulation on the image display unit,
wherein the personalized visible spectrum is a preset obtained by performing a step of photographing a standard group of skin conditions preferred according to the fashion to calculate a mean intensity value for each wavelength,
wherein the step of generating a spectral comparison table comprises storing a data pair comprising W and I in the spectral comparison table by comparing the measured visible spectrum of the skin with the personalized visible spectrum for each wavelength range thereof,
wherein the W of the data pair refers to a wavelength range, and
wherein the I of the data pair refers to a difference value between an intensity of the personalized visible spectrum and an intensity of the measured visible spectrum of the skin in the W,
wherein the step of matching a personalized cosmetic formulation to the spectral comparison table includes matching a component of the personalized cosmetic formulation to at least one data pair stored in the spectral comparison table,
wherein the step of matching a component of the personalized cosmetic formulation includes matching a corresponding wavelength reinforcement material to the W of the at least one data pair stored in the spectral comparison table, and
wherein the wavelength reinforcement material is one wavelength reinforcement powder or two or more wavelength reinforcement composite powders which selected from the group consisting of mica, synthetic mica, alumina, borosilicate powder, talc, and sericite.

\* \* \* \* \*